United States Patent [19]
Kamiyama et al.

[11] 4,120,908
[45] Oct. 17, 1978

[54] PROCESS FOR THE CONVERSION OF $C_8$ AROMATIC HYDROCARBONS

[75] Inventors: Setsuo Kamiyama; Katsumi Kaneko, both of Ooi; Yukio Nagashima, Wako; Hiroshi Furukawa, Ooi; Shozo Wada, Zushi, all of Japan

[73] Assignee: Toa Nenryo Kogyo Kabushiki Kaisha, Tokyo, Japan

[21] Appl. No.: 797,992

[22] Filed: May 18, 1977

[30] Foreign Application Priority Data

Jun. 4, 1976 [JP] Japan .................................. 51-64564

[51] Int. Cl.² ............................................. C07C 15/08
[52] U.S. Cl. ........................... 260/668 A; 208/DIG. 2
[58] Field of Search .............. 260/668 A; 208/DIG. 2

[56] References Cited
U.S. PATENT DOCUMENTS

| | | | |
|---|---|---|---|
| 3,130,006 | 4/1964 | Rabo | 208/DIG. 2 |
| 3,856,872 | 12/1974 | Morrison | 260/668 A |
| 3,856,873 | 12/1974 | Burress | 260/668 A |

*Primary Examiner*—Veronica O'Keefe
*Attorney, Agent, or Firm*—Rebecca Yablonsky

[57] ABSTRACT

A $C_8$ aromatic hydrocarbon mixture which typically may consist essentially of xylenes and ethylbenzene, the latter being present in an amount of not more than 40 weight percent, is converted to a product containing an increased proportion of p-xylene by bringing it into contact with an acid leached hydrogen form mordenite having a silica to alumina mole ratio of 15-21 at a temperature in the range of 180° to 250° C. under a pressure of atmospheric to 200 Kg/cm². Hydrogen may be present in the system in a mole ratio of hydrogen to $C_8$ aromatic hydrocarbon mixture of 0-10. The reaction may be conducted in the vapor phase or in the liquid phase.

10 Claims, No Drawings

PROCESS FOR THE CONVERSION OF $C_8$ AROMATIC HYDROCARBONS

BACKGROUND OF THE INVENTION

1. Field of the Invention

The present invention relates to a process for the conversion of $C_8$ aromatic hydrocarbons and, more particularly, it is concerned with a process for converting or transforming effectively a mixture of $C_8$ aromatic hydrocarbons containing ethylbenzene and xylenes by the use of an acid leached hydrogen type mordenite catalyst having a particular silica/alumina ratio.

2. Description of the Prior Art

Of late, large amounts of $C_8$ aromatic hydrocarbons have been obtained by separation from distillates of coal tar, reformed products or thermally cracked products of petroleum, etc. However, the principal demand for these $C_8$ aromatic hydrocarbons is, in fact, limited to p-xylene and o-xylene and, accordingly, many proposals have hitherto been made on methods of converting the residual $C_8$ aromatic hydrocarbon mixture, from which such xylene isomers have been recovered, into the useful components by isomerization or disproportionation. For example, it is well known that the isomerization of xylene is carried out in a vapor phase reaction at high temperature around 500° C. using a solid acid catalyst, but this method is not practical since the operation must be carried out at a high temperature and the catalyst deteriorates. In order to solve this problem, there have recently been proposed a method comprising using a silica-alumina catalyst in the liquid phase at a temperature of about 290° to 400° C. under high pressure (see Japanese Patent Publication No. 6460/75 based on Japanese application No. 103397 filed Dec. 24, 1969.) and a method comprising carrying out the reaction in the liquid phase at a temperature of 0° to 400° C. using a chromium-containing hydrogen type mordenite catalyst (see Japanese Patent Publication No. 88032/75 assigned to Teijin K.K.). However, these methods also have disadvantages. That is, the former method, aimed at preventing deterioration of the catalyst, still requires a rather high temperature and has an insufficient isomerization efficiency, while the latter method requires a troublesome procedure for the preparation of the catalyst because of the addition of chromium. Other references are Japanese Patent Publication No. 3976/74 based on Japanese application No. 24768 filed May 15, 1969 assigned to Universal Oil Products Co.; Japanese Patent Publication Nos. 53335/75 and 53336/75 assigned to Mobil Oil Corp. and Japanese Patent Publication No. 39632/76 based on Japanese application No. 111646 filed Sept. 30, 1974 assigned to Teijin K.K.

U.S. Pat. No. 3,780,123 assigned to Texaco Inc. discloses a disproportionation method with a composite catalyst starting with, e.g., ethylbenzene, in which, however, no xylenes are produced.

On the other hand, a number of methods for removing ethylbenzene present in high concentration in $C_8$ aromatic hydrocarbons have hitherto been proposed so as to obtain starting materials for the production of p-xylene by isomerization of $C_8$ aromatic hydrocarbons. One of the prior art methods, therefore, is a superfractionation method, which has many disadvantages; for example, it requires a large installation investment and high operating cost on a commercial scale. A hydrogenation and isomerization method using a noble metal catalyst is also known but this method has the disadvantage that the selectivity of ethylbenzene conversion is not as great as desired, resulting in loss of the xylene isomers present with formation of a large amount of non-aromatic hydrocarbons due to hydrogenation. Furthermore, there has recently been proposed a method for the disproportionation of ethylbenzene in the presence of a chlorine compound using only ethylbenzene as starting material and an acid leached hydrogen type mordenite catalyst with a high silica to alumina molar ratio but this method needs the presence of chlorine which has a corrosive action in the reaction system.

SUMMARY OF THE INVENTION

Applicants have made various studies for the purpose of overcoming the above-described disadvantages of the prior art and developing a method whereby isomerization of xylenes in $C_8$ aromatic hydrocarbons and disproportionation of ethylbenzene into other useful constituents, for example, benzene and diethylbenzene, as a means for preventing ethylbenzene from accumulating in the isomerization loop of $C_8$ aromatic hydrocarbons, can be accomplished simultaneously and effectively, and, consequently, have found that these objects can be achieved at a low temperature by using an acid leached hydrogen type mordenite catalyst, the silica to alumina molar ratio of which is adjusted to a particular range. In accordance with the present invention, there is provided a process for the conversion of $C_8$ aromatic hydrocarbons which comprises contacting a mixture of $C_8$ aromatic hydrocarbons with an acid leached hydrogen type mordenite catalyst having a silica to alumina molar ratio of 15 to 21 at a temperature of 180° to 250° C. under a pressure of atmospheric to 200 Kg/cm$^2$.

DETAILED DESCRIPTION OF THE INVENTION

The catalyst used in the present invention can be prepared by converting synthetic or natural mordenite into the hydrogen form in conventional manner and then subjecting it to acid leaching to remove alumina so that the silica to alumina molar ratio ranges from 15 to 21. In detail, the preparation of the catalyst by this acid leaching is carried out by contacting a hydrogen type mordenite with a mineral acid such as hydrochloric acid, nitric acid, sulfuric acid, phosphoric acid or the like at normal temperature or with heating, washing adequately until the anion of the mineral acid used is not detected, drying at a temperature of at least 100° C. and then calcining at 450° to 550° C. in air. The acid leaching can also be carried out simultaneously with the conversion of mordenite into that of the hydrogen type.

The physical properties of the so obtained acid leached hydrogen type mordenite catalyst cannot generally be defined, but it is desirable that the catalyst have a surface area of 400 to 500 m$^2$/g, a pore volume of 0.20 to 0.45 ml/g and an Na$_2$O content of at most 0.05% by weight.

The mixture of $C_8$ aromatic hydrocarbons, used as a starting material in the present invention, may comprise o-xylene, m-xylene, p-xylene and ethylbenzene, the content of ethylbenzene being at least 5% by weight, which composition is not in thermodynamic equilibrium. If the content of ethylbenzene in the starting material exceeds 40% by weight, the isomerization and recovery of xylenes is lowered and, therefore, a content of at most 40% by weight is desirable.

A distinguishing feature of the present invention is to use an acid leached hydrogen type mordenite catalyst having a silica/alumina molar ratio of 15 to 21 and in this range of the silica/alumina molar ratio the disproportionation of ethylbenzene and the isomerization of xylenes proceed in parallel with excellent conversion, which is unobvious from the catalyst systems of the prior art.

The conversion process of the present invention can be carried out either continuously or batchwise and in the case of continuous operation it is preferable to use a fixed bed type or suspension type catalyst. The reaction temperature in this conversion process is preferably in the range of 180° to 250° C., since, if the reaction temperature is lower than this range, conversion is low and if higher than this range, side reactions take place and the selectivity decreases. Up to the present time, it has been believed that, with a catalyst system of this kind, i.e., hydrogen type mordenite, the isomerization of xylenes scarcely takes place at a low temperatue such as below 300° C. It has now been found that, on the contrary, with the catalyst of the present invention the isomerization of xylenes is accomplished even at a low temperature, for example, 180° to 250° C.

The reaction pressure can be selected depending on various reaction conditions, and a reaction pressure ranging from atmospheric pressure to 200 Kg/cm² or more is generally chosen to accomplish the object of the invention. Somewhat elevated pressure conditions are desirable to prolong the catalyst life. The reaction of the present invention can be carried out either in vapor phase or in liquid phase while still obtaining the benefits of the invention. However, the liquid phase reaction results in increased isomerization with less deterioration of the catalyst, i.e., better catalyst life; this effect is much more pronounced than when a hydrogen type mordenite catalyst which has not been leached with acid, thus having a lower silica to alumina molar ratio, is used. Thus the advantages of the present invention are clear.

The liquid hour space velocity (LHSV) in the present invention is 0.1 to 50 hr$^{-1}$, preferably, 0.5 to 10 hr$^{-1}$. In the process of the invention, hydrogen may be present in the reaction system in a proportion of 0 to 10 mols to 1 mol of a mixture of C$_8$ aromatic hydrocarbons.

The present invention will now be illustrated in detail by the following examples.

EXAMPLE 1

A synthetic hydrogen type mordenite having a silica/alumina molar ratio of 12.6 (Commercial Name: Zeolon 200 H, manufactured by Norton Co.) was treated with concentrated hydrochloric acid at room temperature or with heating at 90° C. for a suitable time to leach out a part of the alumina in the mordenite so that a desired composition should be obtained, washed with water until no chlorine ions were found, dried at 110° C. for 2 hours or more and calcined at 500° C. for 6 hours in air, thus obtaining various catalyst having properties as shown in Table I.

A C$_8$ aromatic hydrocarbon mixture of an ethylbenzene/m-xylene ratio of 50/50 by weight was continuously fed to a cylindrical reactor filled with each of these catalysts and reacted at 200° C. and LHSV of 10 hr$^{-1}$ under atmospheric pressure in the presence of hydrogen of 3/1 molar ratio of hydrogen to hydrocarbons. After 1 hour from the start of feeding the hydrocarbons, the reaction product was taken and analyzed to give the results shown in Table I.

It is apparent from the results of Table I that the process of the present invention is excellent.

TABLE I

| Run No. | Silica/Alumina Molar Ratio | Surface Area (m²/g) | Pore Volume (ml/g) | Na$_2$O Content (wt%) | Ethyl-benzene Conversion (%) | Xylenes Isomerization (%)* | Xylenes Recovery (%)** |
|---|---|---|---|---|---|---|---|
| 1 | 12.6 | 346 | 0.13 | 0.32 | 10.0 | — | 94.0 |
| 2 | 14.2 | 368 | 0.19 | 0.09 | 16.5 | 10.8 | 96.0 |
| 3 | 15.0 | 405 | 0.22 | 0.05 | 21.6 | 25.5 | 93.8 |
| 4 | 17.2 | 438 | 0.29 | 0.04 | 26.5 | 30.2 | 92.8 |
| 5 | 20.7 | 498 | 0.43 | 0.04 | 27.3 | 30.1 | 92.9 |
| 6 | 22.7 | 535 | 0.47 | 0.03 | 19.7 | 17.5 | 93.5 |
| 7 | 29.3 | 542 | 0.47 | 0.03 | 16.9 | 11.8 | 97.4 |

NOTES (These definitions are applicable to Tables I-VI)
*% Approach to an Equilibrium Concentration of P-Xylene (0.241) in three Xylene Isomers.
**Recovery of three Xylene Isomers.

EXAMPLE 2

The reactions were conducted at the same conditions as described in Run No. 5 of Example 1 except that the ratio of ethylbenzene to m-xylene was varied, thus obtaining the results shown in Table II. As is evident from the results of Table II, ethylbenzene conversion, xylene isomerization and recovery are increased when using a composition similar to the commonly used starting feed material for isomerization, and the advantage of the present catalyst is thus supported.

TABLE II

| Run No. | Composition of Starting Material (% by Weight) | | Ethyl-benzene Conversion (%) | Xylene Isomerization (%) | Xylene Recovery (%) |
|---|---|---|---|---|---|
| | Ethylbenzene | m-Xylene | | | |
| 8 | 100 | 0 | 25.4 | — | — |
| 5 | 50 | 50 | 27.3 | 30.1 | 92.9 |
| 9 | 22 | 78 | 32.7 | 51.9 | 97.5 |
| 10 | 5 | 95 | 42.1 | 68.2 | 98.9 |

EXAMPLE 3

The reactions were conducted at the same conditions as described in Run No. 9 of Example 2 except for the reaction temperature to thus obtain results shown in Table III. As is evident from the results of Table III, the conversion of ethylbenzene and the isomerization and recovery of xylenes are excellent even at a low temperature, around 200° C.

TABLE III

| Run No. | Reaction Temperature (° C) | Ethyl-benzene Conversion (%) | Xylene Isomerization (%) | Xylene Recovery (%) |
|---|---|---|---|---|
| 11 | 170 | 20.0 | 5.1 | 100 |
| 12 | 185 | 28.0 | 28.8 | 99.8 |
| 9 | 200 | 32.7 | 51.9 | 97.5 |
| 13 | 250 | 53.1 | 89.8 | 93.8 |
| 14 | 270 | 67.2 | 97.2 | 82.8 |

EXAMPLE 4

Using the catalysts used in Example 1, Run Nos. 1, 3, 4, 5, 6 and 7 in a proportion of 1 g per 10 ml of a $C_8$ aromatic hydrocarbon mixture having an ethylbenzene/m-xylene ratio of 22/78 by weight, at 250° C. and a pressure of 30 Kg/cm² for 3 hours under a hydrogen atmosphere in an autoclave (i.e., under the condition of a high pressure-liquid phase), the results shown in Table IV were obtained. As is evident from Table IV, best results are obtained in the range of the silica/alumina ratio according to the present invention even under the reaction condition of high pressure-liquid phase, and better isomerization of xylenes in the reaction under a high pressure-liquid phase is found than under atmospheric pressure-vapor phase.

TABLE IV

| Run No. | Silica/ Alumina Molar Ratio | Ethyl- benzene Conversion (%) | Xylene Isomerization (%) | Xylene Recovery (%) |
| --- | --- | --- | --- | --- |
| 15 | 12.6 | 5.1 | 34.3 | 99.2 |
| 16 | 15.0 | 18.8 | 72.6 | 98.7 |
| 17 | 17.2 | 27.6 | 91.8 | 97.2 |
| 18 | 20.7 | 32.5 | 96.5 | 96.4 |
| 19 | 22.7 | 19.3 | 65.2 | 97.7 |
| 20 | 29.3 | 11.9 | 38.8 | 98.8 |

EXAMPLE 5

The reactions were carried out in liquid phase under pressure in a manner analogous to Example 4 except that the reaction temperature and the ratio of ethylbenzene/m-xylene were changed, thereby obtaining the results shown in Table V.

TABLE V

| Run No. | Reaction Temperature (° C) | Composition of Starting Material Ethylbenzene (%) | m-Xylene (%) | Ethylbenzene Conversion (%) | Xylene Isomerization (%) | Xylene Recovery (%) |
| --- | --- | --- | --- | --- | --- | --- |
| 21 | 250 | 5 | 95 | 40.6 | 97.9 | 97.7 |
| 18 | 250 | 22 | 78 | 32.5 | 96.5 | 96.4 |
| 22 | 235 | 5 | 95 | 31.6 | 89.2 | 98.8 |
| 23 | 235 | 22 | 78 | 22.7 | 80.2 | 96.9 |
| 24 | 235 | 50 | 50 | 19.2 | 69.1 | 94.5 |
| 25 | 200 | 5 | 95 | 19.1 | 68.2 | 99.7 |
| 26 | 200 | 22 | 78 | 8.8 | 54.6 | 97.7 |

EXAMPLE 6

Using an untreated synthetic hydrogen type mordenite catalyst and the acid leached hydrogen type mordenite catalyst of the present invention, a $C_8$ aromatic hydrocarbon mixture having an ethylbenzene/m-xylene ratio of 22/78 by weight was subjected to catalytic reaction under conditions of hydrogen/hydrocarbon molar ratio = 3/1 and LHSV = 1.0 hr⁻¹ in a continuous flow system under an atmospheric vapor phase or in a liquid phase under some pressure, thus obtaining the results shown in Table VI. As is apparent from the results of Table VI, the reaction system in a liquid phase under some pressure is more desirable because of less deterioration of the catalyst activity, and in both the reaction systems of an atmospheric vapor phase and liquid phase under pressure, the catalyst of the present invention is superior to the untreated hydrogen form mordenite.

TABLE VI

| Run No. | Reaction System | Silica/ Alumina Molar Ratio | Reaction Pressure (Kg/cm²) | Reaction Temperature (° C) | Reaction Time (hr) | Ethyl- benzene Conversion (%) | Xylene Isomer- ization (%) | Xylene Recovery (%) |
| --- | --- | --- | --- | --- | --- | --- | --- | --- |
| 27 | Vapor | 12.6 | Atmospheric | 225 | 1 | 24.0 | 50.1 | 98.1 |
| 28 | " | " | " | " | 7 | 13.0 | 27.6 | 99.3 |
| 29 | Vapor | 20.0 | Atmospheric | 200 | 1 | 34.2 | 57.1 | 97.3 |
| 30 | " | " | " | " | 7 | 22.7 | 35.4 | 99.0 |
| 31 | Vapor | 20.0 | 15 | 200 | 6 | 36.8 | 59.3 | 95.5 |
| 32 | " | " | " | " | 25 | 27.5 | 47.0 | 98.8 |
| 33 | Liquid | 12.6 | 50 | 250 | 6 | 22.8 | 67.8 | 95.9 |
| 34 | " | " | " | " | 25 | 15.1 | 42.3 | 96.6 |
| 35 | Liquid | 20.0 | 50 | 225 | 4 | 32.5 | 96.0 | 95.1 |
| 36 | " | " | " | " | 100 | 31.9 | 96.1 | 94.9 |

What is claimed is:

1. A process for the conversion of $C_8$ aromatic hydrocarbons to isomerize xylenes present which comprises contacting a mixture of $C_8$ aromatic hydrocarbons with an acid leached hydrogen form mordenite catalyst having a silica ($SiO_2$) to alumina ($Al_2O_3$) molar ratio of 15 to 21 at a temperature of 180° to 250° C. under a pressure of atmospheric to 200 Kg/cm².

2. The process as set forth in claim 1 wherein the mordenite has been leached with hydrochloric acid.

3. The process as set forth in claim 1 wherein the catalyst has a surface area of 400 to 500 m²/g, a pore volume of 0.20 to 0.45 ml/g and an $Na_2O$ content of not more than 0.05% by weight.

4. The process as set forth in claim 1 wherein the feed mixture contains ethylbenzene.

5. The process as set forth in claim 4 wherein the feed contains 5–40 weight percent ethylbenzene.

6. The process as set forth in claim 1, being carried out in the liquid phase.

7. The process as set forth in claim 1, being carried out in the vapor phase.

8. A process for the conversion of $C_8$ aromatic hydrocarbons which comprises contacting a mixture of $C_8$ aromatic hydrocarbons containing xylenes and containing ethylbenzene which is present in a concentration of 5 to 40 weight percent, to isomerize the xylenes and to convert at least a portion of the ethylbenzene to disproportionated products, with an acid leached hydrogen form mordenite catalyst having a silica to alumina mole ratio of 15–21 in the presence of hydrogen in a mole ratio of hydrogen to $C_8$ aromatic hydrocarbon mixture of about 3:1 at a temperature of 180° to 250° C. in the liquid phase under a pressure of 30–50 Kg/cm² and recovering a product containing an increased proportion of p-xylene.

9. The process as set forth in claim 1, being carried out in the presence of hydrogen.

10. The process as set forth in claim 9, the molar proportion of hydrogen to $C_8$ aromatic hydrocarbon mixture being not greater than 10.

* * * * *